(12) United States Patent
Taranta et al.

(10) Patent No.: US 8,840,909 B2
(45) Date of Patent: Sep. 23, 2014

(54) MULTIPURPOSE ANT BAIT

(75) Inventors: Claude Taranta, Stutensee (DE);
Thomas Bork, Westhofen (DE);
Gerhard Schnabel, Elsenfeld (DE);
Helmut Müller, Weisenheim (DE);
Sarah Thompson, Raleigh, NC (US);
Clark D. Klein, Pittsboro, NC (US);
Nigel Armes, Raleigh, NC (US); Tiffany Hennessey, Wake Forest, NC (US)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 13/130,654

(22) PCT Filed: Nov. 16, 2009

(86) PCT No.: PCT/EP2009/065186
§ 371 (c)(1),
(2), (4) Date: May 23, 2011

(87) PCT Pub. No.: WO2010/060817
PCT Pub. Date: Jun. 3, 2010

(65) Prior Publication Data
US 2011/0236451 A1 Sep. 29, 2011

Related U.S. Application Data

(60) Provisional application No. 61/117,681, filed on Nov. 25, 2008.

(30) Foreign Application Priority Data

Dec. 16, 2008 (EP) ..................................... 08171820

(51) Int. Cl.
*A01N 25/34* (2006.01)
*A01N 25/00* (2006.01)
*A01N 43/56* (2006.01)
*A01N 47/34* (2006.01)

(52) U.S. Cl.
CPC .............. *A01N 25/006* (2013.01); *A01N 43/56* (2013.01); *A01N 47/34* (2013.01)

USPC ........... 424/408; 424/409; 424/410; 514/407; 514/590

(58) Field of Classification Search
None
See application file for complete search history.

(56) References Cited

U.S. PATENT DOCUMENTS

| 4,834,977 | A | 5/1989 | Kohama et al. |
| 6,682,755 | B1 | 1/2004 | Chuhran |
| 6,939,830 | B1 * | 9/2005 | Gaulliard et al. .............. 504/253 |
| 7,045,138 | B2 * | 5/2006 | Kennedy et al. .............. 424/406 |
| 2002/0042439 | A1 | 4/2002 | Zangiacomi |
| 2006/0142157 | A1 | 6/2006 | Birthisel et al. |

FOREIGN PATENT DOCUMENTS

| EP | 0 295 442 | 12/1988 |
| EP | 0 575 838 | 12/1993 |
| FR | 2050908 | 4/1971 |
| JP | 08-175910 | 7/1996 |
| JP | 09-059104 | 3/1997 |
| JP | 11-092301 | 4/1999 |
| WO | WO 01/17354 | 3/2001 |
| WO | WO 01/76372 | 10/2001 |
| WO | WO 2007/010095 | 1/2007 |

OTHER PUBLICATIONS

International Search Report prepared in International Application No. PCT/EP2009/065186, filed Nov. 16, 2009.
International Preliminary Report on Patentability from corresponding International Application No. PCT/EP2009/065186, filed Nov. 16, 2009.

* cited by examiner

*Primary Examiner* — Neil Levy
(74) *Attorney, Agent, or Firm* — Brinks Gilson & Lione

(57) ABSTRACT

Subject of the present invention is a solid ant bait comprising an insecticide and a bait composition. Another subject is a process for the preparation of said ant bait, comprising extruding a mixture, which contains the insecticide and the bait composition. Yet another subject is a method for controlling ants, comprising offering to said ants the ant bait according to the invention. Finally, a subject is a use of the ant bait according to the invention for controlling ants.

16 Claims, No Drawings

MULTIPURPOSE ANT BAIT

This application is a National Stage application of International Application No. PCT/EP2009/065186, filed Nov. 16, 2009, which claims the benefit of U.S. Provisional Application No. 61/117,681, filed Nov. 25, 2008, the entire contents of which are hereby incorporated herein by reference. This application also claims priority under 35 U.S.C. §119 to European Patent Application No. 08171820.7, filed Dec. 16, 2008, the entire contents of which are hereby incorporated herein by reference.

Subject of the present invention is a solid ant bait comprising an insecticide and a bait composition. Another subject is a process for the preparation of said ant bait, comprising extruding a mixture, which contains the insecticide and the bait composition. Yet another subject is a method for controlling ants, comprising offering to said ants the ant bait according to the invention. Finally, a subject is a use of the ant bait according to the invention for controlling ants.

Combinations of preferred embodiments with other preferred embodiments are within the scope of the present invention.

It is often very desirable to control ant populations to prevent painful stings to humans and animals or eliminate the general nuisance caused by some species. The inconvenience caused to individuals by the presence of ants in living areas or in the immediate vicinity thereof, such as in the garden or on the patio can be a major concern. The presence of ants around a house or other structure may be particularly unpleasant for the resident because of the bites inflicted by certain species or general nuisance. The control of ants is also desirable regarding the cultivation of fruit trees and/or ornamentals. Certain species of ants play a role in defending aphids against their predators which contributes toward maintaining high populations of aphids, which are harmful to the health of the trees and/or to fruit yields. The pharaoh ant may create nests inside living areas, which, in the case of blocks of flats and hospitals, may pose hygiene problems.

Ant baits and methods for controlling ants using ant baits are known. U.S. 02/0042439 discloses a method for controlling a population of social insects, such as ants, with a bait and an insecticide, such as fipronil. WO 2001/17354 discloses an insecticidal composition comprising an insecticide, moisture retaining agent and vegetable meal. U.S. Pat. No. 6,682,755 discloses a method for killing insects, comprising preparation of a cellulose spent grain, mixing said grain with a binding substance and an insect attractant, pelletizing and drying said mixture. U.S. Pat. No. 4,834,977 discloses a bait composition in tablet form for the control of insects comprising an insecticide, crystalline cellulose, crop product powders and a saccharide. EP 0 575 838 discloses a pesticidal granular composition comprising a flour material having a vegetal origin and an active ingredient, said composition having certain physical parameters. WO 2007/010095 discloses an insecticidal bait composition in paste form comprising boric acid, alum, potassium sorbate, wheat flour, sugar, onion, milk powder, glycerin citric acid and water. EP 0295442 discloses a non-particulating insecticidal bait composition comprising a toxicant, a liquid sugar, a protein composition and a polymeric binder.

However, these ant baits and methods are not always satisfactory to provide control. The reason for this is that they often destroy only a small portion of the population concerned, for example, in the case of ants, a fraction of the workers whose function is to collect food outside the nest. The destruction of this casteis not, however, sufficient to overcome the drawbacks caused by the ants. Indeed, the ability of ants to proliferate and their specialization based on the needs of the nest are capable of rapidly compensating for this destruction, bringing about an increase in the population. The known methods moreover have the drawback that it is very difficult to treat all the individuals of the population, especially because nests are fairly inaccessible, since they are generally located at a depth of several tens of centimeters below the surface of the ground.

Another disadvantage of known ant baits is they are rather specific to certain ant species. Usually, various species of ants live in an area, in which said ants need to be controlled. Each species has preferences for food. Known ant baits are attractive to certain species and may not be attractive to the complex present. As a result, only populations of certain species are controlled which may not include all of them. Similarly, the manufacturers of ant baits have to produce specific bait compositions for various regions of the world, depending on the ant species in the respective region. Moreover, the ant bait should be easy and safe to handle, especially it should not be dusty to avoid contamination of the persons who apply it. Another disadvantage of known ant baits is that they are in non-solid state, such as gel, paste or putty, resulting in the need for special application equipment or tending to flow away at elevated temperatures.

Object of the present invention was to identify an ant bait which overcomes the aforementioned drawbacks. For example, an object was to identify an ant bait, which was able to control a large portion of the ant population. Further on, an object was to find an ant bait, which was similarly attractive to various ant species. Yet another object was to identify a process for producing an ant bait, which is suitable for industrial mass production and which yields an ant bait, which is safe and easy to handle.

The object was achieved by a solid ant bait comprising an insecticide and a bait composition, wherein the bait composition comprises
   a) from 5 to 95 wt % vegetable flour, and
   b) from 1 to 60 wt % protein source, and
   c) from 5 to 60 wt % sugar, and
   d) from 0.1 to 10 wt % polymeric binder,
each wt % referring to the bait composition.

The ant bait comprises an insecticide. The term "insecticide" within the meaning of the invention states that one or more insecticide can be selected. Preferably, one or two, insecticides are selected. The skilled artisan is familiar with such insecticides, which can be, for example, found in the Pesticide Manual, 13th Ed. (2003), The British Crop Protection Council, London. Examples for insecticides are:

organo(thio)phosphates: acephate, azamethiphos, azinphos-methyl, chlorpyrifos, chlorpyrifos-methyl, chlorfenvinphos, diazinon, dichlorvos, dicrotophos, dimethoate, disulfoton, ethion, fenitrothion, fenthion, isoxathion, malathion, methamidophos, methidathion, methyl-parathion, mevinphos, monocrotophos, oxydemeton-methyl, paraoxon, parathion, phenthoate, phosalone, phosmet, phosphamidon, phorate, phoxim, pirimiphos-methyl, profenofos, prothiofos, sulprophos, tetrachlorvinphos, terbufos, triazophos, trichlorfon;
   carbamates: alanycarb, aldicarb, bendiocarb, benfuracarb, carbaryl, carbofuran, carbosulfan, fenoxycarb, furathiocarb, methiocarb, methomyl, oxamyl, pirimicarb, propoxur, thiodicarb, triazamate;
   pyrethroids: allethrin, bifenthrin, cyfluthrin, cyhalothrin, cyphenothrin, cypermethrin, alpha-cypermethrin, beta-cypermethrin, zeta-cypermethrin, deltamethrin, esfenvalerate, etofenprox, fenpropathrin, fenvalerate, imiprothrin, lambda-cyhalothrin, permethrin, prallethrin, pyrethrin I and II, resmethrin, silafluofen, tau-fluvalinate, tefluthrin, tetramethrin, tralomethrin, transfluthrin, profluthrin, dimefluthrin;

insect growth regulators: a) chitin synthesis inhibitors: benzoylureas: chlorfluazuron, cyramazin, diflubenzuron, flucycloxuron, flufenoxuron, hexaflumuron, lufenuron, novaluron, teflubenzuron, triflumuron; buprofezin, diofenolan, hexythiazox, etoxazole, clofentazine; b) ecdysone antagonists: halofenozide, methoxyfenozide, tebufenozide, azadirachtin; c) juvenoids: pyriproxyfen, methoprene, fenoxycarb; d) lipid biosynthesis inhibitors: spirodiclofen, spiromesifen, spirotetramat;

nicotinic receptor agonists/antagonists compounds: clothianidin, dinotefuran, imidacloprid, thiamethoxam, nitenpyram, acetamiprid, thiacloprid, 1-(2-chloro-thiazol-5-ylmethyl)-2-nitrimino-3,5-dimethyl-[1,3,5]triazinane;

GABA antagonist compounds: endosulfan, ethiprole, fipronil, vaniliprole, pyrafluprole, pyriprole, 5-amino-1-(2,6-dichloro-4-methyl-phenyl)-4-sulfinamoyl-1H-pyrazole-3-carbothioic acid amide;

macrocyclic lactone insecticides: abamectin, emamectin, milbemectin, lepimectin, spinosad, spinetoram;

mitochondrial electron transport inhibitor (METI) I acaricides: fenazaquin, pyridaben, tebufenpyrad, tolfenpyrad, flufenerim;

METI II and III compounds: acequinocyl, fluacyprim, hydramethylnon;

Uncouplers: chlorfenapyr;

oxidative phosphorylation inhibitors: cyhexatin, diafenthiuron, fenbutatin oxide, propargite;

moulting disruptor compounds: cryomazine;

mixed function oxidase inhibitors: piperonyl butoxide;

sodium channel blockers: indoxacarb, metaflumizone;

others: benclothiaz, bifenazate, cartap, flonicamid, pyridalyl, pymetrozine, sulfur, thiocyclam, flubendiamide, chlorantraniliprole, cyazypyr (HGW86), cyenopyrafen, flupyrazofos, cyflumetofen, amidoflumet, imicyafos, bistrifluron, and pyrifluquinazon.

Typically, an insecticide especially effective for controlling ants is selected. Preferably, the insecticide is metaflumizone, fipronil, or metaflumizone and fipronil.

In another preferred embodiment the insecticide is selected from the group of pyrethroids, GABA antagonist compounds, sodium channel blocker compounds, nicotinic receptor agonists/antagonists compounds, and uncoupler compounds. Particular preferred compositions contain at least one insecticide compound selected from the group consisting of bifenthrin, tefluthrin, α-cypermethrin, lambda cyhalotrin, ethiprole, pyriprole, fipronil, metaflumizone, acetamiprid, clothianidin, imidacloprid, nitenpyram, thiacloprid, thiamethoxam, dinetofuran, and chlorfenapyr.

In another preferred embodiment, the insecticide is selected from the group of pyrethroids, in particular selected from bifenthrin, tefluthrin, α-cypermethrin or lambda cyhalotrin.

In another preferred embodiment, the insecticide is selected from the group of GABA antagonist compounds, in particular selected from ethiprole, pyriprole and fipronil.

In a further preferred embodiment, the insecticide is selected from the group of sodium channel blocker compounds, in particular metaflumizone.

In a further preferred embodiment, the insecticide is selected from the group of nicotinic receptor agonists/antagonists compounds, in particular selected from acetamiprid, clothianidin, imidacloprid, nitenpyram, thiacloprid, thiamethoxam and dinetofuran.

A further preferred embodiment, the insecticide is selected from the group of uncoupler compound, in particular chlorfenapyr.

The vegetable flour may be prepared by milling of grains or cereals from wheat, barley, rye, oats, rice, sorghum, soybeans, corn, garbanzo or amaranth. Also potato flour may be used. Vegetable flours may have the form of powders, usually with a particle size from 10-1000 µm, preferably from 50 to 500 µm. Suitable wheat flour is for example of flour type 405, 1050 or 1150. Preferred vegetable flour is corn flour or wheat flour, especially wheat flour.

The sugar may be any known monosaccharide or disaccharide or mixtures thereof, preferably those which are available from natural sources. Examples are saccharose (sucrose), glucose, lactose, fructose, dextrose, maltose. Technical mixtures comprising sugar may also be used, such as black sugar, brown sugar, honey, molasses. Preferably, the sugar is a disaccharide, more preferably saccharose.

The polymeric binder has typically the function of an extrusion aid. Preferred polymeric binders are polyvinylpyrrolidone and polysaccharides. Preferred polysaccharides are cellulose derivatives, preferably cellulose derivatives that are usually prepared by chemical, polymer analogous reactions of cellulose. Preferred cellulose derivatives are cellulose esters, such as cellulose acetate or cellulose butyrate, and cellulose ethers, such as carboxymethyl cellulose, methyl cellulose, methylhydroxyalkyl cellulose, hydroxyethyl cellulose, carboxymethyl hydroxyethy cellulose, ethyl cellulose, ethyl hydroxyethyl cellulose, hydroxypropyl cellulose. More preferred polymeric binder are cellulose ethers, especially methyl cellulose.

The protein source is usually a composition comprising polyamino acids from natural or synthetic origin, preferably from natural origin. Typically, the protein source has a crude protein content of at least 10 wt %, preferably at least 20 wt %, more preferably at least 30 wt %, even more preferably at least 40 wt % and most preferably at least 50 wt % based on dry matter of the protein source. The crude protein content may be determined by known methods, which are generally suitable for the respective protein source. Preferably, the crude protein content is determined by the Kjeldahl method for the crude protein content, such as DIN EN ISO 5983-1 "Animal feeding stuffs—Determination of nitrogen content and calculation of crude protein content. Part 1: Kjeldahl method" from October 2005. For plant protein, the DIN EN ISO 20483 "Cereals and pulses—Determination of nitrogen content and calculation of crude protein content—Kjeldahl method" from February 2007 is especially preferred. For milk proteins, the ISO TS 17837 EN "Milk and milk products—Determination of nitrogen content and calculation of crude protein content—Kjeldahl method" from March 2008 is especially preferred. Examples of proteins from natural sources are milk proteins (such as casein, sodium casein, calcium casein, lactalbumin, dried milk), plant protein (such as gluten, e.g. from wheat; soy extract, peanut extract, zein), animal protein (such as fish meal, meat meal, egg white, liver powder (e.g. from chicken liver or poultry liver), collagen, dried insects, such as crickets) or yeast. Preferred protein is milk protein and animal protein, more preferably animal protein, and especially dried insects.

The bait composition may additionally comprise glycol. The glycol is usually an C2 to C12 alkane substituted with two or three hydroxy groups. Suitable examples of glycols are 1,2-ethane diol, 1,2-propane diol, 1,3-propane diol, glycerol, 1,4-butandiol. Preferred glycols are 1,2-propane diol and glycerol.

The bait composition may additionally comprise water, such as tap water or distilled water.

The bait composition may comprise further additives, for example an anti-oxidizing agent, a preservative, a coloring agent, a flavoring agent or a feed attractant. Such additives are usually added in amounts, which are well known to the expert.

Examples of the anti-oxidizing agent are erythorbic acid, sodium erythorbate, di-tert-butyl hydroxytoluene (BHT), dl-alpha-tocophelol, nordihydroguaiaretic acid, methylhydroxyanisole, propyl gallate, guaiac resin, L-cysteine hydrochloride.

Examples of the preservative are benzoic acid, sodium benzoate, salicylic acid, diphenyl, sorbic acid, potassium sorbate, dehydroacetic acid, sodium dehydroacetate, isobutyl p-oxybenzoate, isopropyl p-oxybenzoate, ethyl p-oxybenzoate, butyl p-oxybenzoate, propyl p-oxybenzoate, calcium propionate, sodium propionate, 2-methyl-4-isothiazolin-3-one (MIT), 1,2-benzisothiazolin-3-one (BIT) (mixtures of MIT and BIT are commercially available as Acticide® MBS from Thor), 1,2-Benzisothiazolin-3-one, 2-Bromo-2-nitro-propane-1,3-diol or 2-Methyl-3(2H)-isothiazolone (mixtures of the latter three compounds are commercially available as acticide MBL 5515 from Thor).

Examples of a coloring agent is a dye or a pigment, such as Rhodamin B, C.I. Pigment Red 112, C.I. Solvent Red 1, pigment blue 15:4, pigment blue 15:3, pigment blue 15:2, pigment blue 15:1, pigment blue 80, pigment yellow 1, pigment yellow 13, pigment red 112, pigment red 48:2, pigment red 48:1, pigment red 57:1, pigment red 53:1, pigment orange 43, pigment orange 34, pigment orange 5, pigment green 36, pigment green 7, pigment white 6, pigment brown 25, basic violet 10, basic violet 49, acid red 51, acid red 52, acid red 14, acid blue 9, acid yellow 23, basic red 10, basic red 108, amaranth, amaranth aluminium lake, erythrosine, erythrosine aluminium lake, new coccine, Phloxine, rose bengal, acid eed, tartrazine, tartrazine aluminium lake, Sunset Yellow FCF, Sunset Yellow FCF aluminium lake, Fast Green FCF, Fast Green FCF aluminium lake, Brilliant Blue FCF, Brilliant Blue FCF aluminium lake, indigo carmine, indigo carmine aluminium lake, beta-carotene, copper chlorophyll.

Examples of the flavoring agent are cheese flavor, butter flavor, peanut flavor, peach flavor, strawberry flavor, milk flavor.

Examples of the feed attractant are essential oils such as soybean oil, rapeseed oil, sesame oil, cotton seed oil, wheat germ oil, corn oil, sunflower oil, palm oil, castor oil and linseed oil.

The solid ant bait according to the invention may comprise from 0.01 to 5 wt % insecticide, preferably from 0.05 to 2.5 wt %, more preferably from 0.1 to 1 wt %, relative to the ant bait.

The bait composition comprises a) from 5 to 95 wt % vegetable flour, b) from 1 to 60 wt % protein source, c) from 5 to 60 wt % sugar, and d) from 0.1 to 10 wt % polymeric binder, each wt % refering to the bait composition. In a preferred embodiment, the bait composition comprises a) from 5 to 95 wt % vegetable flour, b) from 1 to 60 wt % protein source, c) from 5 to 60 wt % sugar, d) from 0.1 to 10 wt % polymeric binder, and e) from 0.5 to 15 wt % glycol, each wt % refering to the bait composition.

The bait composition may comprise from 5 to 95 wt % vegetable flour, preferably from 5 to 40 wt %, more preferably from 5 to 20 wt %. In an embodiment ("high protein bait"), the solid ant bait may comprise from 5 to 30 wt % vegetable flour, preferably from 10 to 25 wt %, more preferably from 15 to 22 wt %. In another embodiment ("low protein bait") the solid ant bait may comprise from 30 to 80 wt % vegetable flour, preferably from 35 to 70 wt %, more preferably from 40 to 65 wt %. The aforementioned wt % refer each to the bait composition.

The bait composition may comprise from 1 to 60 wt % protein source, preferably from 1 to 50 wt %, more preferably from 5 to 40 wt %. In an embodiment ("high protein bait"), the solid ant bait may comprise from 10 to 60 wt % protein source, preferably from 20 to 50 wt %, more preferably from 30 to 45 wt %. In another embodiment ("low protein bait") the solid ant bait may comprise from 1 to 30 wt % protein source, preferably from 2 to 20 wt %, more preferably from 3 to 10 wt %. The aforementioned wt % refer each to the bait composition.

The bait composition may comprise from 5 to 60 wt % sugar, preferably from 10 to 50 wt %, more preferably from 15 to 40 wt %, relative to the bait composition.

The bait composition may comprise from 0.1 to 10 wt % polymer binder, preferably from 1.0 to 3.0 wt %, more preferably from 1.5 to 2.5 wt %, relative to the bait composition.

The bait composition may comprise from 0.5 to 15.0 wt % glycol, preferably from 2 to 10 wt %, more preferably from 3 to 7 wt %, relative to the bait composition. In another preferred embodiment, the bait composition may comprise up to 15.0 wt % glycol, preferably up to 10 wt %, more preferably up to 7 wt %, relative to the bait composition.

The bait composition may comprise from 1.0 to 15.0 wt % water, preferably from 2 to 12.5 wt %, more preferably from 6.0 to 10.0 wt %, relative to the bait composition. In another preferred embodiment, the bait composition may comprise up to 15.0 wt % water, preferably up to 12.5 wt %, more preferably up to 10.0 wt %, relative to the bait composition. The water content may be determined by methods known in the art, for example Karl-Fischer titration or weighting out before and after drying, e.g. in a vacuum oven at elevated temperature.

The bait composition may comprise from 0.01 to 1.0 wt % preservative, preferably from 0.05 to 0.5 wt %, more preferably from 0.1 to 0.3 wt %, relative to the bait composition.

In another preferred embodiment, the bait composition may comprise up to 1.0 wt % preservative.

In an embodiment of the invention, the bait composition comprises a) from 5 to 40 wt % vegetable flour, and b) from 1 to 60 wt % protein source ("high protein bait"). Preferably, the bait composition comprises
  a) 5 to 30 wt % vegetable flour,
  b) 10 to 60 wt % protein source,
  c) 30 to 50 wt % sugar, and
  d) 0.5 to 4 wt % polymeric binder.
More preferably, the bait composition comprises
  a) 5 to 20 wt % wheat flour,
  b) 25 to 40 wt % crickets powder,
  c) 35 to 45 wt % saccharose, and
  d) 1.0 to 3.0 wt % methyl cellulose.

In another preferred embodiment, the bait composition comprises
  a) 5 to 30 wt % vegetable flour,
  b) 10 to 60 wt % protein source,
  c) 30 to 50 wt % sugar,
  d) 0.5 to 4 wt % polymeric binder, and
  e) up to 15 wt % glycol.
The aforementioned wt % refer each to the bait composition.

In another embodiment of the invention the bait composition comprises a) from 30 to 80 wt % vegetable flour, and b) from 1 to 30 wt % protein source ("low protein bait").

Preferably, the bait composition comprises
a) 30 to 80 wt % vegetable flour,
b) 1 to 30 wt % protein source,
c) 30 to 50 wt % sugar, and
d) 0.5 to 4 wt % polymeric binder.

More preferably, the bait composition comprises
a) 40 to 65 wt % wheat flour,
b) 3 to 10 wt % crickets powder,
c) 35 to 45 wt % saccharose, and
d) 1.0 to 3.0 wt % methyl cellulose.

In another preferred embodiment, the bait composition comprises
a) 30 to 80 wt % vegetable flour,
b) 1 to 30 wt % protein source,
c) 30 to 50 wt % sugar,
d) 0.5 to 4 wt % polymeric binder, and
e) up to 15 wt % glycol.

The aforementioned wt % refer each to the bait composition.

The amounts of various components of the bait composition may be selected in such a manner, that a solid ant bait results. Typically, the amounts of the components add up or may be filled up with other formulation additives to 100 wt %. Regarding the attractiveness to ants of the bait composition, it is well known in the art that there is no difference between baits containing insecticide or without insecticide.

The ant baits according to the invention may be prepared by a process comprising extruding a mixture, which contains the insecticide and the bait composition. Usually, the process further comprises drying of the extruded or pelleted mixture, preferably extruded. Preferably, the ant bait according to the invention is obtained by extrusion of a mixture comprising the insecticide and the bait composition.

In a preferred embodiment, the process comprises mixing the insecticide and the components of the bait composition to form a paste with a water content of 25 to 55 wt %, preferably 30 to 45 wt %, and extruding the mixture. The expert will adjust the water content in order to achieve an extrudable texture of the paste. Extruders are well known in the art. For example, a one screw or twin screw extruder may be used. Also extruders used for producing spaghetti may be used. Typically, the extrusion is accomplished at a pressure (usually taken just before entering into the extrusion grid) from 1 to 80 bars, preferably from 1 to 60 bars, and more preferably from 1 to 40 bars. Typically, the extrusion is accomplished at a temperature from 10 to 100° C., preferably from 20 to 80° C., and more preferably from 30 to 60° C. Said temperature refers to the paste during extrusion. When necessary, the temperature is maintained at the desired value by cooling. An extrusion grid may be used with holes of any shape, preferably of circular shape. Typically, the diameter of the holes is from 0.2 to 5.0 mm, preferably from 0.5 to 3 mm, more preferably from 0.5 to 2.0 mm.

The extrudate may be dried to lower the water content of the extrudate. Drying may be done by the application of elevated temperatures, such as hot air, from 30 to 150° C., preferably from 50 to 80° C. The heating time depends on the temperature, the size of the extrudate and the desired amount of water in the final product.

The stick-like extrudate may be cut, e.g. with a rotating knife, into shorter sticks before or after drying, preferably before drying. In the case of circular holes, the spaghetti-shaped extrudate may be cut into cylindrical shape. In case of polygonal holes (e.g. triangular or rectangular), the extrudate may be cut into corresponding shapes. The resulting pellets might be broken into shorter granules before or after drying, preferably after drying. Preferably, the resulting granules have cylindrical shape with a length of 0.2 to 2 mm and a diameter of 0.2 to 2 mm. In another preferred embodiment, the resulting granules have a shape, which has length of 0.2 to 2 mm at its most distant points, and a diameter of 0.2 to 2 mm at its broadest diameter.

The ant bait according to the invention is a solid ant bait. Preferably, the solid ant bait is a solid granule. These granules may have a shape, which has length of 0.2 to 2 mm at its most distant points, and a diameter of 0.2 to 2 mm at its broadest diameter. The expert clearly differentiates between a solid bait and a non-solid bait, such as a liquid, a gel, a past or a putty. Usually, solid state of matter is characterized by a distinct structural rigidity and virtual resistance to deformation (that is changes of shape and/or volume). Usually, solids have high values both of Young's modulus (e.g. at least 0.1 GPa) and of the shear modulus of elasticity (e.g. at least 0.01 GPa).

In another aspect of the invention, a method is provided for controlling ants, comprising offering to said ants the ant bait according to claims 1 to 8. Preferably, the ants are selected from Argentine ants (*Linepithema humile*), Big-headed ants (*Pheidole* spp.), Odorous house ant (*Tapinoma sessile*), Fire ants (*Solenopsis* spp.), Crazy ants (*Paratrechina* spp.) and *Lasius* spp. More preferably, at least two species of ants, which are present in the same area and are selected from Argentine ants (*Linepithema humile*), Big-headed ants (*Pheidole* spp.), Odorous house ant (*Tapinoma sessile*), Fire ants (*Solenopsis* spp.), Crazy ants (*Paratrechina* spp.) and *Lasius* spp., are controlled.

Populations of ants may be controlled using the method according to the invention. Control of a population of ants is understood to mean the control of the said insects, and more particularly the total or almost total destruction of the said population, in other words the destruction of more than 60%, preferably more than 70% and even more preferably of 95 to 100%, of the said population. The population of ants which may be controlled using the ant bait according to the invention is a population of ants living in the same nest. In this case, the minor fraction of the population to which the ant bait is applied generally consists of workers whose function is to collect food from outside the nest, these being known as the workers of the nest.

An effective amount of the composition used in the method according to the invention is understood to mean an amount which is capable of controlling the whole population of ants. More particularly, the invention relates to a method for treating ants with an effective amount of the ant bait according to the invention, this effective amount of composition being an amount used equal to the dose required to destroy at least 90% of the minor fraction of the population of social insects to which the said composition is applied, within a period of between 2 and 30 days, preferably between 2 and 7 days. The minor fraction often corresponds in practice to the population living or circulating outside the common dwelling place or nest. Typically, an effective dose is between 0.0001 and 20 grams per 100 m$^2$, of one or more areas frequented by, or assumed to be frequented by, the said ants, the said area being outside the place of the said common dwelling but being a place in which the ants circulate or are assumed to circulate.

The solid ant bait may be applied by various methods, such as broadcasting it over a large area or by a bait carrier box. The preferred application method is broadcast over a large area.

Thus, foraging ants outside of the nest may pick up the bait and return it to the nest where the toxicant is passed to other colony members.

A further aspect of the invention relates to a use of the ant bait according to the invention for controlling ants. Preferably, the ants are selected from Argentine ants (*Linepithema humile*), Big-headed ants (*Pheidole* spp.), Odorous house ant (*Tapinoma sessile*), Fire ants (*Solenopsis* spp.), Crazy ants (*Paratrechina* spp.) and *Lasius* spp. More preferably, at least two species of ants, which are present in the same area and are selected from Argentine ants (*Linepithema humile*), Big-headed ants (*Pheidole* spp.), Odorous house ant (*Tapinoma sessile*), Fire ants (*Solenopsis* spp.), Crazy ants (*Paratrechina* spp.) and *Lasius* spp. are controlled.

The present invention offers various advantages: The ant bait according to the invention, is similarly attractive to various ant species. The process according to the invention, especially the extrusion process for producing the ant bait, is suitable for industrial mass production. The process yields an ant bait, which is safe, easy to handle and dust-free. The ant bait can be utilized worldwide with available machinery. Another advantage is the solid state of the ant bait, which allows strewing of the ant bait by hand or with the help of strewing devices. Further on, solid ant baits are much easier to handle and apply compared to gels, pastes or putties. Even in warmer climates or application zones the solid baits remain in their desired shape and can easily take away by the ants in this shape.

The invention is further illustrated but not limited by the following examples.

EXAMPLES

Methyl cellulose: cellulose ether made from cellulose and methyl chloride, aqueous viscosity 3.5 to 4.7 (at 2 wt % analyzed according to Brookfield RVT at 20° C. and 20 rpm, on bone-dry basis), commercially available under as Culminal® MC3000P from Hercules.

Crickets: Freeze dried crickets, milled to a particle size below 1 mm.

Wheat flour: Common wheat flour Type 405.

Example 1

High protein Ant Bait (Prototype 1)

Following components were mixed at room temperature in a mixer:
30 wt % crickets
40 wt % saccharose
2.0 wt % methyl cellulose
5.0 wt % 1,2-propylenglycol
6.0 wt % water
16.8 wt % wheat flour
0.2 wt % sodium benzoate The composition were extruded either with an AFREM or with a Fuji-Paudal extruder (monovis) at a room temperature under a pressure of 1 to 40 bars. The extrudate was dried at 50° C. The water content was of the ant bait was 6 wt %. The resulting pellets are broken down or sieved to shorter size. The resulting granules had a cylindrical shape with a diameter of 0.5 to 0.75 mm and a length of 0.5 to 0.75 mm.

Example 2

Low Protein Ant Bait (Prototype 2)

Following components were mixed at room temperature:
5.0 wt % crickets
40 wt % saccharose
2.0 wt % methyl cellulose
5.0 wt % 1,2-propylenglycol
6.0 wt % water
41.8 wt % wheat flour
0.2 wt % sodium benzoate The mixture was extruded, dried, sieved as described in example 1.

Example 3

Field Test of the Attractiveness of Blank Baits

The field tests were conducted with various ants species at various locations as listed in Table 1. In each test 30 bait granules were put in an area near a nest or other heavy ant activity. The containers containing the different bait granules were randomly placed equidistant to the ants, so that the conditions for bait removal were equal. Each test was replicated four times with different nests each time. The amount of time required to remove all 30 bait granules was recorded. Table 2 lists the mean number of minutes until the ants removed all 30 bait granules.

For comparison, a commercially available granular ant bait ("Control 1") was used named Maxforce® Professional Insect Control Granular Insect Bait from Bayer Crop Science comprising 1 wt % Hydramethylnon, or an ant bait ("Control 2"), which was composed of corn grit (35 wt %), sugar (40 wt %), soybean oil (20 wt %) and additives (5 wt %).

Protype baits in Example 1 and 2 are very attractive to all the tested ants species. Further on, the average mean time across all ant species for bait removal was 12.68 min (Prototype 1 bait), 14.64 minutes (Prototype 2 bait), 18.22 min (Control 2), and 24.07 min (Control 1). These experiments showed that the ant bait according to the invention are similarly attractive to various ant species all over the world.

TABLE 1

Field test systems

| Test Nr. | Ant | Ant | Field test in |
|---|---|---|---|
| 1 | Tropical fire ant | *Solenopsis geminata* | Pingtung, Taiwan |
| 2 | Red imported fire ant 1 | *Solenopsis invicta* | Orlando, FL, USA |
| 3 | Red imported fire ant 2 | *Solenopsis invicta* | Holly Springs, NC, USA |
| 4 | Caribean crazy ant | *Paratrechina pubens* | Vero Beach, FL, USA |
| 5 | Argentine ant 1 (June) | *Linepithema humile* | Modesto, CA, USA |
| 6 | Argentine ant 1 (August) | *Linepithema humile* | Modesto, CA, USA |
| 7 | Argentine ant 1 (October) | *Linepithema humile* | Modesto, CA, USA |
| 8 | Argentine ant 2 | *Linepithema humile* | Research Triangel Park, NC, USA |
| 9 | Argentine ant 3 | *Linepithema humile* | San Luis Obispo, CA, USA |
| 10 | Argentine ant 4 | *Linepithema humile* | Arroyo Grande, CA, USA |
| 11 | Argentine ant 5 | *Linepithema humile* | Orlando, FL, USA |
| 12 | California Harvester Ant | *Pogonomyrmex californicus* | Dinuba, CA, USA |
| 13 | Black garden ant | *Lasius niger* | Louhossoa, France |
| 14 | Coastal brown ant | *Pheidole megacephala* | Holloways Beach, Australia |
| 15 | Odorous house ant | *Tapinoma nigerrimum* | Utrera, Spain |

TABLE 2

Results of tests

| Nr. | Removal time [min] for Prototype 1 | Removal time [min] for Prototype 2 | Removal time [min] for Control 1[1)] | Removal time [min] for Sweet Ant Bait[1)] |
|---|---|---|---|---|
| 1 | 5.13 | 9.5 | 4.13 | 12.13 |
| 2 | 12.5 | 16.25 | 5 | 29 |
| 3 | 12.25 | 21.75 | 8.25 | 28.25 |
| 4 | 5.75 | 9.5 | 30 | 30 |
| 5 | 27 | 29 | 27 | 30 |
| 6 | 21.5 | 24 | 28.75 | 30 |
| 7 | 23.3 | 26.7 | 25 | 30 |
| 8 | 5 | 7 | 8 | 30 |
| 9 | 16.25 | 18.75 | 30 | 30 |
| 10 | 12 | 15 | 30 | 30 |
| 11 | 11.5 | 14.5 | 26.25 | 30 |
| 12 | 14.7 | 18.4 | 11.5 | 10.9 |
| 13 | 9.5 | 13 | 22.5 | 22.5 |
| 14 | 10.25 | 10.75 | 15 | 15 |
| 15 | 3.63 | 4.25 | 1.88 | 3.25 |

[1)]not according to the invention

The invention claimed is:

1. A process for the preparation of an ant bait comprising extruding a mixture which contains an insecticide and a bait composition, wherein the bait composition comprises:
   a) from 5 to 95 wt % vegetable flour,
   b) from 1 to 60 wt % protein source,
   c) from 5 to 60 wt % sugar, and
   d) from 0.1 to 10 wt % polymeric binder,
      each wt % referring to the bait composition,
   wherein the bait is a solid granule,
   wherein the polymeric binder is selected from polyvinylpyrrolidone and polysaccharides, or mixtures thereof,
   wherein the solid granules comprise a shape having a length of 0.2 to 2 mm and a diameter of 0.2 to 2 mm,
   wherein the protein source is dried insects, and
   wherein the sugar is a monosaccharide, a disaccharide, or mixtures thereof, and wherein the polysaccharide of the polymeric binder is a cellulose ester or a cellulose ether.

2. The process of claim 1, wherein the extrusion is accomplished at a pressure from 1 to 80 bars.

3. The process of claim 1, wherein the ant bait has a cylindrical shape.

4. The process of claim 1, wherein the insecticide is metaflumizone, fipronil, or metaflumizone and fipronil.

5. The process of claim 1, wherein the polymeric binder comprises cellulose esters.

6. The process of claim 1, wherein the polymeric binder comprises methyl cellulose.

7. The process of claim 1, wherein the protein source is crickets.

8. The process of claim 1, wherein the bait composition comprises 1.0 to 15.0 wt % water.

9. An ant bait obtained by the process of claim 1.

10. A method for controlling ants, comprising offering the ant bait of claim 9.

11. The method of claim 10, wherein at least two species of ants selected from the group consisting of Argentine ants (*Linepithema humile*), Big-headed ants (*Pheidole* spp.), Odorous house ant (*Tapinoma sessile*), Fire ants (*Solenopsis* spp.), Crazy ants (*Paratrechina* spp.) and *Lasius* spp. are controlled.

12. The method of claim 11, wherein the bait composition comprises:
   a) from 30 to 80 wt % of the vegetable flour, and
   b) from 1 to 30 wt % of the protein source,
      each wt % referring to the bait composition.

13. The method of claim 11, wherein the bait composition comprises:
   a) from 5 to 30 wt % of the vegetable flour, and
   b) from 10 to 60 wt % of the protein source,
      each wt % referring to the bait composition.

14. The method of claim 11, wherein the bait composition additionally comprises up to 1 wt % preservative, relative to the bait composition.

15. The method of claim 11, wherein the ant bait has cylindrical shape.

16. The method of claim 11, wherein the insecticide is metaflumizone, fipronil, or metaflumizone and fipronil.

* * * * *